(12) United States Patent
Miller et al.

(10) Patent No.: US 7,631,981 B2
(45) Date of Patent: Dec. 15, 2009

(54) DISPOSABLE MEDICAL-EXAMINATION LIGHT

(75) Inventors: Jonathan Miller, Willard City, UT (US); Ben Shirley, Salt Lake City, UT (US); Mark Fox, Sandy, UT (US)

(73) Assignee: Utah Medical Products, Inc., Midvale, UT (US)

( * ) Notice: Subject to any disclaimer, the term of this patent is extended or adjusted under 35 U.S.C. 154(b) by 109 days.

(21) Appl. No.: 11/872,200

(22) Filed: Oct. 15, 2007

(65) Prior Publication Data

US 2009/0097236 A1 Apr. 16, 2009

(51) Int. Cl.
*B25B 23/18* (2006.01)
*A61B 1/32* (2006.01)

(52) U.S. Cl. .................. 362/119; 362/804; 362/191; 600/223

(58) Field of Classification Search .................. 362/202, 362/206, 399, 109, 804, 572; 600/223, 84, 600/197, 198, 199
See application file for complete search history.

(56) References Cited

U.S. PATENT DOCUMENTS

| | | | | |
|---|---|---|---|---|
| 5,580,147 A | * | 12/1996 | Salerno | 362/551 |
| 5,716,329 A | * | 2/1998 | Dieter | 600/210 |
| 5,785,408 A | * | 7/1998 | Tseng | 362/119 |
| 5,797,670 A | * | 8/1998 | Snoke et al. | 362/119 |
| 6,019,482 A | * | 2/2000 | Everett | 362/184 |
| 6,379,296 B1 | * | 4/2002 | Baggett | 600/178 |
| 6,428,180 B1 | * | 8/2002 | Karram et al. | 362/119 |
| 6,510,918 B2 | * | 1/2003 | Bates | 181/131 |
| 7,036,627 B2 | * | 5/2006 | Costa et al. | 181/131 |
| 7,284,981 B2 | * | 10/2007 | Schmid et al. | 433/29 |
| 2004/0099266 A1 | * | 5/2004 | Cross et al. | 128/203.12 |
| 2004/0107610 A1 | * | 6/2004 | Gulati | 40/316 |

* cited by examiner

*Primary Examiner*—Ali Alavi

(57) ABSTRACT

The present invention relates to a disposable medical-examination light. Specifically, the invention relates to a disposable light for use with a speculum. Generally, the disposable light includes a casing with an interior and an exterior. The casing interior may be adapted to hold at least one battery. The casing exterior may include a proximal surface and a distal surface. A protrusion may extend from the proximal surface, and at least one light-emitting diode ("LED"), such as a white and/or green light producing LED, may be substantially disposed at a proximal end of the protrusion. Additionally, a gripping mechanism may extend from the casing's proximal surface. The disposable light may also comprise electrical components for connecting at least one battery to at least one LED. Furthermore, the disposable light may also include a switching mechanism that may be configured to close an electrical circuit between an LED and a battery.

23 Claims, 4 Drawing Sheets

DISPOSABLE MEDICAL-EXAMINATION LIGHT

BACKGROUND OF THE INVENTION

This application relates generally to a disposable medical-examination light. More specifically, this application relates to a disposable vaginal speculum light.

In order to non-surgically examine and treat an interior body cavity it is often necessary to use an instrument that dilates the cavity. Often specula of different varieties are used for this purpose. However, once an interior cavity has been dilated with a speculum, it may be necessary to light or illuminate the cavity before the cavity can be properly examined, treated, tested, diagnosed, etc.

There are many instruments and methods that can be used to provide light to a dilated interior cavity. For instance, light may be provided to a cavity by a gooseneck lamp; a handheld light; a standing lamp; an exterior light source used with a reflector placed on the head of a user (e.g., an examiner) or in some other location; a light source incorporated with, or connected to, the speculum; and so forth.

However, such instruments may have several shortcomings. For instance, some instruments used to light interior cavities may be handheld and thereby may limit the use or otherwise occupy one of the hands of the user. Similarly, the size and shape of some conventional lighting instruments may cause the instruments to be cumbersome and awkward to use. Some lighting instruments may significantly obstruct the user's visual/working field. Conversely, in some cases, the user may unintentionally block the light from a lighting instrument with medical instruments, the user's body parts, or with some other object. Moreover, in another example of potential shortcomings in current medical-examination lights, some lighting instruments, such as incandescent lamps, may become hot and, therefore, may not be placed close to the interior cavity without burning or uncomfortably heating the area being examined. Additionally, some lights may produce a dull yellow or a low intensity light that may strain the user's eyes or may distort the colors of the internal cavity, which may prevent true color visualization.

In addition to these shortcomings, many conventional lighting instruments used to provide light to interior cavities may also face the challenge of being sterile or at least being sanitary enough to be used multiple times on different people. For instance, some methods for cleaning or sterilizing lighting instruments may result in instrument or battery damage. However, other methods for keeping lighting instruments sanitary enough that the instruments may be used to light internal cavities from multiple people may involve covering the lighting instrument with a transparent plastic covering or bag. Nevertheless, transparent coverings may also have their shortcomings. For example, the coverings may make it difficult to handle a lighting instrument, or the coverings may rip or be moved to expose unsanitary portions of the lighting instrument.

Accordingly, it may be an improvement in the art to provide a medical-examination light for illuminating internal cavities, where the light is easy to use, minimally obstructive, and/or provides truer color visualization without uncomfortable amounts of heat. Furthermore, it may be an improvement to provide a medical-examination light that does not require cleaning or transparent coverings because the examination light is disposable after a single use.

BRIEF SUMMARY OF THE INVENTION

This application relates to a disposable medical-examination light. Generally the disposable light includes a casing adapted to hold a power source and at least one light-emitting diode ("LED"). The casing may have an interior and an exterior. The interior of the casing may be adapted to hold the power source. The exterior of the casing may include a proximal surface and a distal surface. A protrusion may extend from the proximal surface, within which is disposed the at least one light-emitting diode ("LED").

Additionally, a disposable gripping mechanism may extend from the proximal surface of the casing. The gripping mechanism may be used to attach the disposable light to an object, such as a speculum. In some cases, the gripping mechanism may include a first resilient grip member that opposes an adjacent second grip member formed on the protrusion. The first and second grip members may have a frictional engagement, such as a barb, that may help retain the disposable light on an object. The grip members may further allow the protrusion to minimally extend into the user's visual/working field.

The disposable light may further comprise electrical components for connecting at least one LED to a power source, such as one or more batteries. Furthermore, the disposable light may also include a disposable switching mechanism that may be configured to close an electrical circuit between the power source and the LED(s). One example of such a switching mechanism may include a non-conductive pull tab that is removably placed within the electrical circuit.

In some instances, the disposable light may include a single LED that produces light of a desired wavelength. For example, the LED may produce white light, green light, or any other desired wavelength of light. In other instances, the disposable light may include two or more LEDs. In one embodiment, the disposable light may include both a green light and a white light producing LED. Where the disposable light includes more than one LED, the light may include a switching mechanism that may be used to switch between powering the various lights.

Such a disposable light may provide better visualization, produce less heat, occlude less of the visual/working field, be easier to use, and/or be more sanitary than some other conventional lights.

BRIEF DESCRIPTION OF THE DRAWINGS

The following description can be better understood in light of several Figures, in which.

Figure 1:
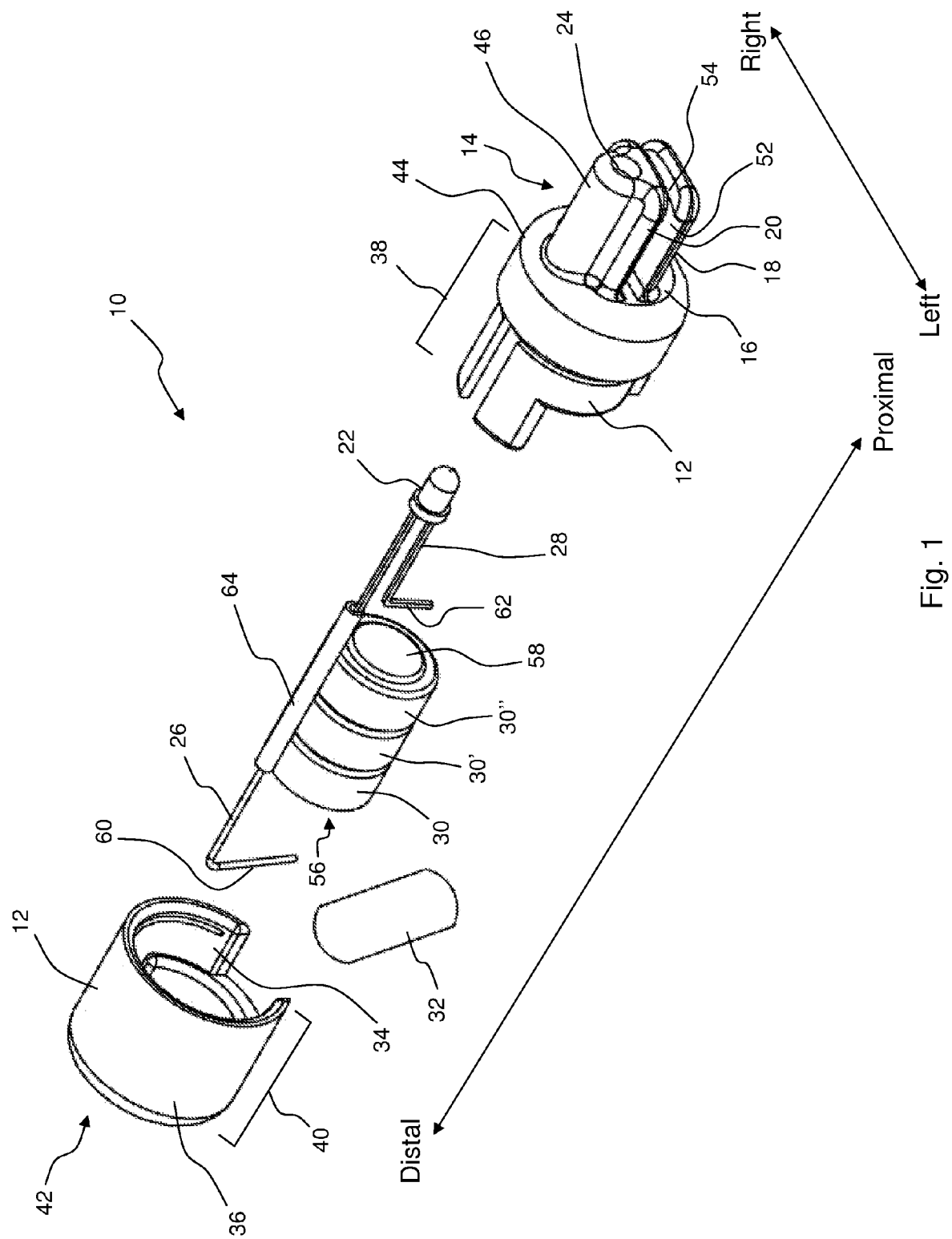
FIG. 1 contains an exploded view of one embodiment of a disposable medical-examination light.

Together with the following description, the Figures help demonstrate and explain certain principles of the invention and methods for making and using the invention. In the Figures, the thickness and configuration of components may be exaggerated for clarity. The same reference numerals in different Figures may represent the same component.

DETAILED DESCRIPTION OF THE INVENTION

The presently preferred embodiments of the described invention may be understood by reference to the following description. It will be appreciated that the components of the described invention, as generally described herein, may be arranged and designed in a wide variety of different configurations. Thus, the following more detailed description of the embodiments of the present invention is not intended to limit the scope of the invention, as claimed, but is merely representative of presently preferred embodiments of the invention. Moreover, while the following discussion focuses on implementing the described invention with a speculum, the skilled artisan will recognize that the described invention may be implemented in any other desired application. For instance, the invention may be attached to any medical device or apparatus to provide localized light. Similarly, while the following description discusses using the described invention to provide light to internal cavities, the skilled artisan will recognize that the invention may be used to provide light to any desired object.

This application relates generally to a disposable medical-examination light. In particular, this application relates to a disposable speculum light that may be used to provide light to an internal cavity, for any desired purpose (e.g., examination, treatment, diagnosis, testing, etc.). The described disposable light may be used with any type of speculum. For instance, the disposable light may be used with an ear speculum, a nasal speculum, an anal speculum, and so forth. However, in order to better explain the implementation of the disposable examination light, this application describes the use of the disposable light in the non-limiting embodiment of a disposable medical-examination light used with a vaginal speculum.

Figure 2A:
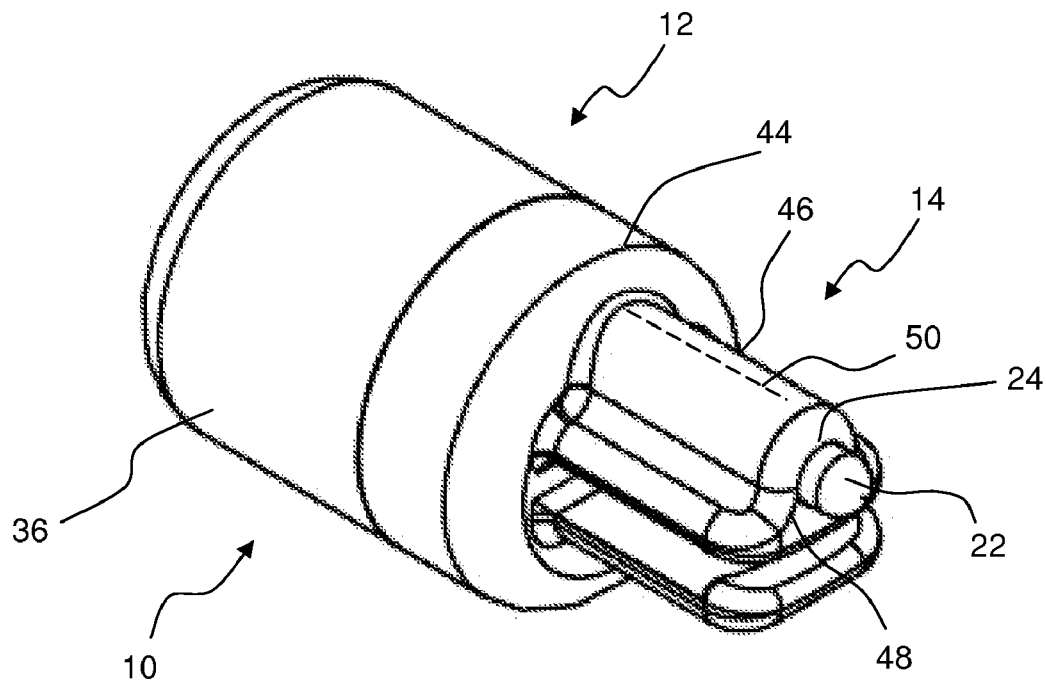
FIGS. 2A and 2B show a perspective view of one embodiment of a disposable medical-examination light.
Figure 2B:
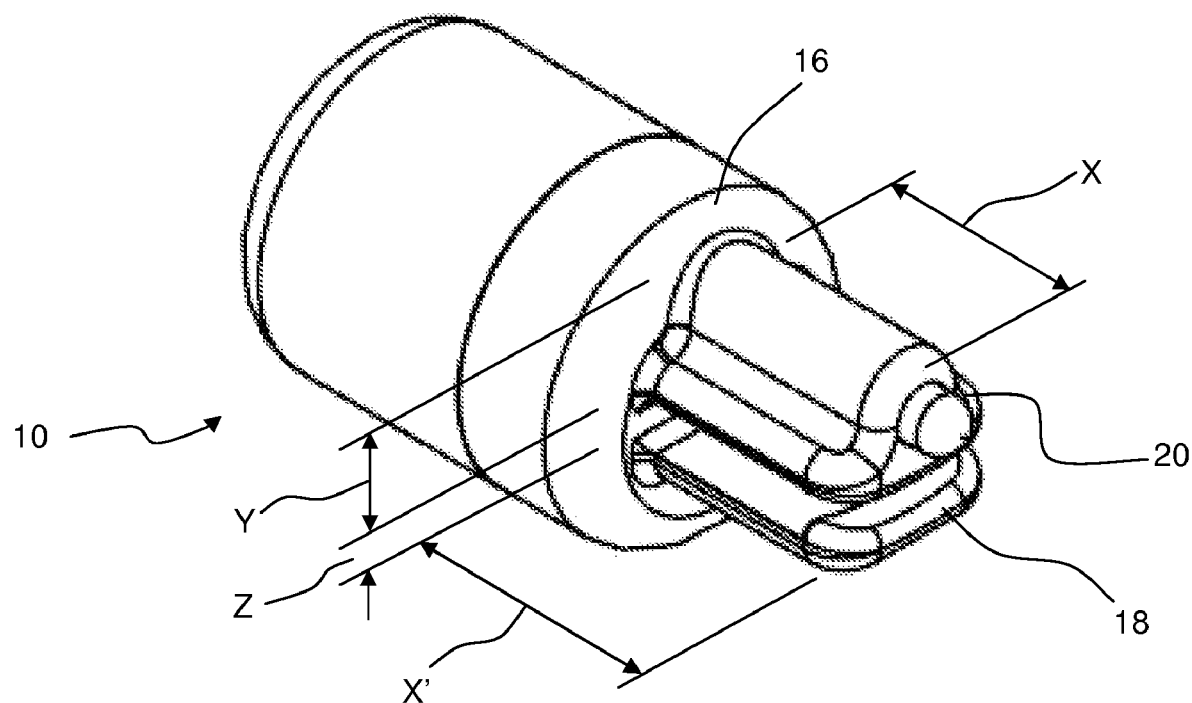

Although the disposable medical-examination light shown in FIGS. 1, 2A, and 2B may include any desired component, those Figures illustrate that, in some embodiments, the disposable light 10 may comprise a casing 12 with a protrusion 14 extending from a proximal surface 16 of the casing 12. Similarly, FIG. 1 illustrates that the disposable light 10 may have a gripping mechanism, such as the first grip member 18 and the second grip member 20, that extends from the proximal surface 16. In this embodiment, one or more light-emitting diodes ("LED" or "LEDs"), such as the LED 22 in FIG. 1, may be substantially disposed within a hollow opening 24 that may be defined by the protrusion 14. Furthermore, the disposable light 10 may include electrical components. These components, such as the wires 26 and 28 depicted in FIG. 1, may serve to connect the LED(s) to a power source, such as one or more batteries, as depicted in FIG. 1 by 30, 30', and 30". The disposable light 10 may also have a switching mechanism that may be configured to close an electrical circuit between the LED(s) and the power source. One non-limiting example of a switching mechanism depicted in FIG. 1 is the pull tab 32. To better explain the disposable light 10, each of the aforementioned components is discussed below in more detail.

For instance, FIG. 2A illustrates that, in some embodiments, the disposable light 10 may include a casing 12. The casing 12 is sized and configured to hold a power source, an LED(s), and/or electrical components. Moreover, the casing 12 may also have any desired characteristic or component. For example, FIG. 1 illustrates that the casing 12 may comprise an interior 34 and an exterior 36. Furthermore, FIG. 1 shows that, in some embodiments, the casing 12 may have a proximal portion 38 and a distal portion 40. The proximal portion 38 may have the proximal surface 16 at the proximal end thereof. Conversely, the distal portion 40 may have a distal surface 42 at the distal end thereof.

Indeed, the interior 34 and the exterior 36 casing 12 may be shaped to allow the casing 12 to hold the power source, the LED(s), and/or electrical components (which are described hereinafter) while being minimally obstructive to the user's visual/working field. For example, the interior 34 and/or the exterior 36 of the casing 12 may be substantially cylindrical, cuboidal, or of any other desired shape. Additionally, the interior 34 of the casing 12 may be sized to fit tightly around the power source. For instance, FIG. 1 illustrates that the interior 34 of the casing 12 may be substantially cylindrical in shape so as to substantially match the shape of the power source (e.g., batteries 30, 30', and 30"). However, in another embodiment within the scope of the invention, the interior 34 of the casing 12 may be shaped to hold the power source in a different configuration. For instance, the batteries 30, 30', and 30" may be configured inside the casing 12 so that the batteries 30, 30', and 30" set side by side, as opposed to being stacked upon each other, as illustrated in FIG. 1. Indeed, such an embodiment may further decrease the amount of the casing 12 that obstructs to the user's visual/working field.

In yet another example of casing 12 shape, the interior 34 and the exterior 36 of the casing 12 may be substantially similar in shape and size. In FIG. 1 the substantially cylindrical space defined by the interior 34 is concentric with the slightly larger substantially cylindrical shape of the exterior 36 of the casing 12. Such a casing 12 may be slightly larger than the power source disposed in the interior 34, and may thereby only occlude a minimal amount of the visual/working field.

In some embodiments, the casing 12 may hold one or more LEDs, such as the LED 22 in FIG. 1, in its proximal surface 16. Further, the LED 22 may be substantially disposed in any desired location in the proximal surface 16. For instance, the LED 22 may be disposed in the center of the proximal surface 16 or the LED 22 may be located off center near a perimeter 44 of the proximal surface 16. Where the LED 22 is located off center in the proximal surface 16, the LED 22 may have any desired location or orientation. For example, the LED 22 may be located closer to the perimeter 44 of the proximal surface 16 than to the center of the proximal surface 16. Indeed, placing the LED(s) near the perimeter 44 of the proximal surface 16 may be beneficial because it allows less of the casing 12 to occlude the user's visual/working field, as is described below.

In other embodiments, one or more LEDs may be substantially disposed in the protrusion 14 that may extend from the casing 12. Although the protrusion 14 may extend from any part of the casing 12, FIG. 1 depicts that, in some embodiments, the protrusion 14 may extend from the proximal surface 16 of the casing 12. Additionally, the protrusion 14 may extend from any location on the proximal surface 16. For instance, the protrusion 14 may extend from the center of the proximal surface 16, or the protrusion 14 may extend from the perimeter 44 of the proximal surface 16. For example, FIG. 1 illustrates the protrusion 14 extending from the proximal surface 16, adjacent to the perimeter 44 of the proximal surface 16. Furthermore, the protrusion 14 may extend from the proximal surface 16 at any desired angle. For example, as illustrated in FIG. 1, the protrusion 14 may extend substantially perpendicular to the proximal surface 16.

The protrusion 14 may also have any desired characteristic that allows one or more LEDs to be disposed at a proximal end thereof, while being minimally obstructive to the user's visual/working field. As used herein with reference to the protrusion 14, the term proximal end may include a portion of the protrusion 14 that is located adjacent to or on the most proximal part of the protrusion 14, as shown in FIG. 1. In one example of a characteristic of the protrusion 14, in some embodiments, the protrusion 14 may be hollow or define one or more openings, such as the opening 24 in FIG. 1. The opening 24 may serve any purpose, including allowing the LED 22 to be substantially disposed in the protrusion 14. The opening 24 defined by the protrusion 14 may also have any desired characteristic. For instance, the opening 24 may have any shape, size, diameter, length, width, or other characteristic that allows the LED 22 to be substantially disposed therein. FIG. 2A, for example, illustrates that the LED 22 may be substantially disposed within the opening 24 of the protrusion 14 and may extend slightly from the protrusion 14.

In another example of a possible characteristic of the protrusion 14, in some embodiments, the protrusion 14 may be formed to allow one or more LEDs to be disposed on or near a surface of the protrusion 14. In this embodiment, the wires 26 and 28 may extend through the protrusion 14 and enter the interior 34 of the casing 12. In yet another example of a possible characteristic of the protrusion 14, the protrusion 14 may be substantially deformable, malleable, rigid, or resilient, depending on the application. For example, a protrusion 14 that is substantially deformable may allow the protrusion 14 to be bent so as to point the LED in a desired direction.

The protrusion 14 may be any shape that allows the protrusion 14 to be minimally obstructive to the user's visual/working field. For example, the protrusion 14 may be substantially cylindrical, cuboidal, semi-spherical, or have any other desired shape. For instance, FIG. 1 depicts that the protrusion 14 may have a portion 46 that is substantially cylindrical or semi-cylindrical in appearance that may be joined or formed with the second grip member 20. The protrusion 14 may also serve many purposes. For example, such a protrusion 14 may serve as part of the gripping mechanism (described hereinafter) and may, thereby, allow the LED 22 to be close to the gripping mechanism so that only the protrusion 14 and a minimal amount of the casing 12 extend into the visual/working field.

Similarly, the protrusion 14 may be of any size suitable for use with a disposable examination light 10. For example, FIGS. 2A and 2B show that the length X of the protrusion 14, as measured from the proximal surface 16 of the casing 12 to the proximal tip 48 of the protrusion 14, may be any suitable distance for use with a speculum. For instance, the length X of the protrusion 14 may be as short as about 0 millimeters or as long as about 3 centimeters. In one example, the protrusion 14 may have a length X between about 0.5 and about 2 centimeters. In another example, the protrusion 14 may have a length X between about 1 centimeter and about 1.4 centimeters. For instance, the protrusion 14 may have a length X of about 1.4 centimeters.

In another example of protrusion size, the protrusion 14 may have any diameter or height that allows it to be minimally obstructive to the user's visual/working field. For instance, a substantially cylindrical protrusion may have any suitable diameter, or a substantially conical protrusion may have any range of diameters that allows the protrusion 14 to be minimally obstructive to the visual/working field. Further, as FIGS. 2A and 2B depict, a protrusion 14 that is joined to the second grip member 20 may have a height Y, where the height Y may be measured from the edge 50 (represented by a dotted line) of the substantially cylindrical-shaped portion 46 to the interior face of the second grip member 20 (or the portion of the second grip member 20 that faces the opposing first grip member 18). For example, the height Y of the protrusion 14 may be as small as about 3 millimeters or as large as about 18 millimeters. In another example, the protrusion 14 may have a height Y of less than about 8 millimeters. In yet another example, the height Y of the protrusion 14 may be between about 4 and about 6 millimeters. Indeed, in one embodiment, the protrusion 14 may have a height Y of about 5 millimeters.

Figure 3:
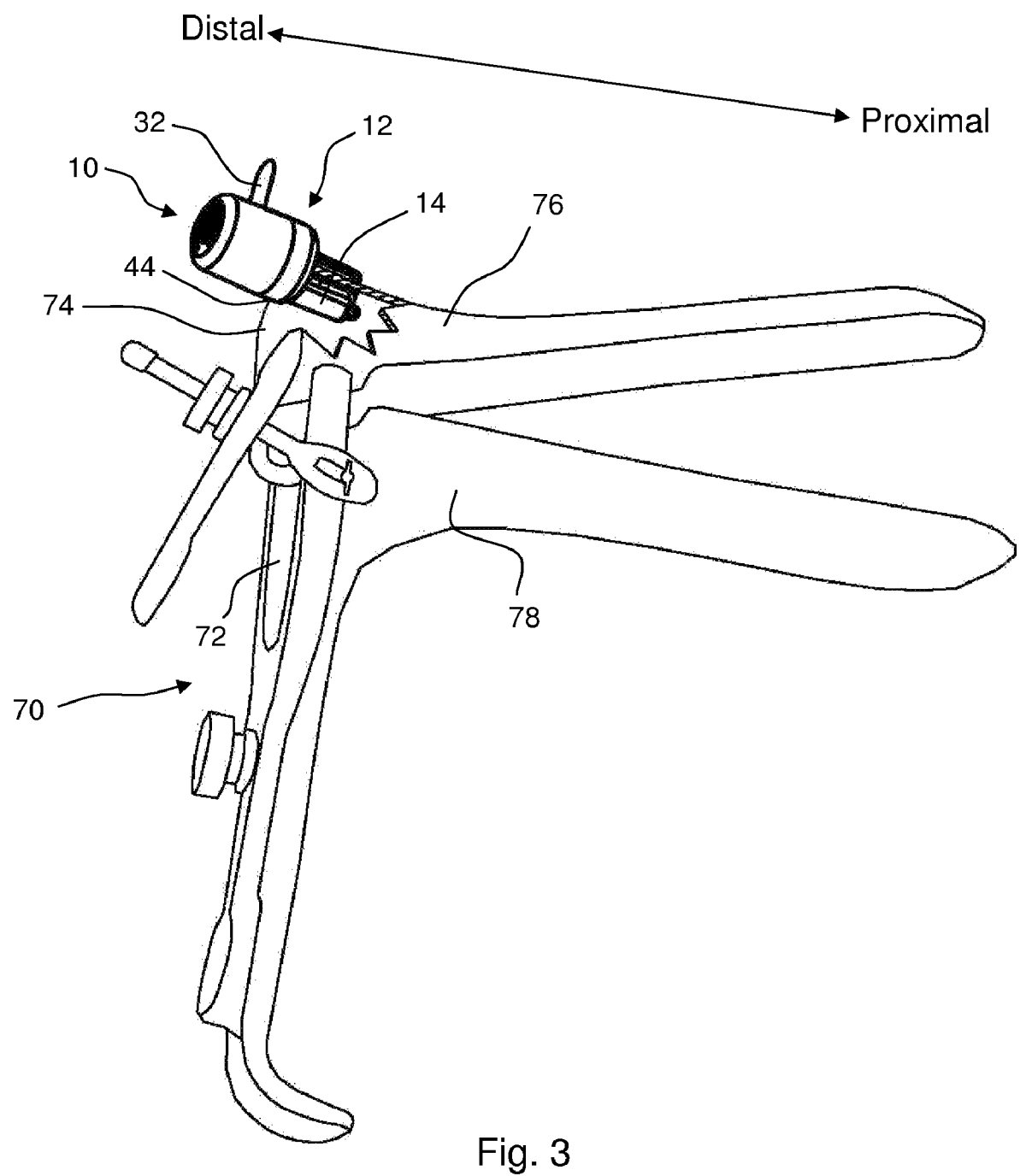
FIG. 3 contains a perspective view of a speculum with a portion of a blade cutaway to show one embodiment of a disposable medical-examination light attached to the speculum.

The protrusion's height Y and placement on the proximal surface 16 may allow the disposable examination light 10 to obstruct a minimal amount of the visual/working field that may be defined by the speculum 70. For instance, FIG. 3 illustrates that in embodiments where the protrusion 14 extends from the proximal surface 16 adjacent to or at a perimeter 44 of the proximal surface 16, the protrusion 14 and a similar amount of the casing 12 may extend into the visual/working field 72 of the speculum 70. The visual/working field 72 includes the space at the distal end 74 of the speculum 70, between the speculum blades 76 and 78. In this example, the protrusion 14 extends into the visual/working field 72 approximately the distance of the height Y of the protrusion 14. For instance, where the height Y of the protrusion 14 is less than about 6 millimeters, the protrusion 14 and a corresponding portion of the casing 12 may only extend into the visual/working field 72 of the speculum 70 about 6 millimeters.

FIG. 1 illustrates that, in some embodiments, a gripping mechanism may extend from the proximal face 16 of the casing 12. In such embodiments, the disposable light 10 may include any gripping mechanism that is suitable to connect the casing 12 to a desired object, such as a speculum. Some examples of a suitable gripping mechanism may include two opposing grip members, one grip member opposing the protrusion 14, or any other known or novel components used for connecting the casing 12 to an object. For example, FIG. 1 depicts that the gripping mechanism may comprise a first grip member 18 that opposes an adjacent second grip member 20, which may be formed on or as part of the protrusion 14.

Where the gripping mechanism comprises one or more grip members, such as the first 18 and second 20 grip members in FIG. 1, the grip members 18 and 20 may have any desired characteristic to render them effective at attaching the light 10 to an object. For example, one or more of the grip members 18 and 20 may be resilient, include a frictional engagement, include different component for connecting to the casing 12 (e.g., pivotal connector and spring), or have any other characteristic suitable to aid the grip members 18 and 20 in attaching the casing 12 to any object. For instance, the first grip member 18 may be resilient. Thus, the first grip member 18 may bend from its initial position and return to allow an object to be inserted, retained, and/or removed from between the first 18 and second 20 grip members.

As mentioned, the grip members 18 and 20 may further comprise a frictional engagement. Any engagement that provides friction between a grip member 18 or 20 and another object may be used. For example, the interior face 52 (as depicted in FIG. 1) of the first grip member 18 may have a texture, such as a knurled or rough texture; material, such as a nitrile polymer or a rubber; or shape, such as a barb; that allows the grip members 18 and/or 20 to be retained on an object. For instance, FIG. 1 depicts that at least the first grip member 18 may have a barb 54 that acts as a frictional engagement. Such a barb 54 may have a shape or size to facilitate attachment to an object, such as a speculum. Furthermore, the barb 54 may be configured to match contours of a speculum 70. For example, one or more barbs 54 may be shaped to match the curvature of the distal end 74 a speculum blade 76.

The grip members 18 and 20 may be sized to attach the disposable light 10 to an object, while being minimally obstructive to the user's visual/working field. For example, the grip members 18 and 20 may have a length, width, or thickness that allows the grip members to be minimally obstructive to the user's visual/working field. FIG. 2B illustrates, for instance, that the grip members 18 and 20 may have a length X' substantially equal to that of the protrusion 14, where X' may be measured as the distance between the proximal surface 16 and the most proximal part of the grip members 18 and 20. FIG. 1 also depicts that, in some embodiments, the grip members 18 and 20 may extend to the left or right of the semi-cylindrical portion 46 of the protrusion 14.

The grip members 18 and 20 may extend from the proximal surface 16 of the casing 12 at a location that allows the disposable light 10 to light a desired area, while being minimally obstructive to the user's visual/working field. For instance, FIG. 1 illustrates that the first grip member 18 may extend roughly from the center of the proximal surface 16. FIG. 1 further illustrates that the interior surface 52 of the first grip member 18 may face or run substantially parallel to the interior surface (not shown) of the second grip member 20. Because the second grip member 20 is formed on the protrusion 14, and the protrusion 14 is adjacent to the perimeter 44 of the proximal surface 16, the second grip member 20 may extend from the proximal surface 16, off from the center of the proximal surface 16. Thus, the protrusion 14 connected to the second grip member 20 may extend into the visual/working field 72 of the speculum 70, while the first grip member 18 and the remaining portion of the proximal surface may remain out of the visual/working field 72.

FIG. 2B also illustrates that the first 18 and the second 20 grip members may be spaced from each other by any separation distance Z suitable to allow an object to be inserted, retained, and/or removed from between the gripping members 18 and 20. For example, the grip members 18 and 20 may be spaced with a separation distance Z of about 8 millimeters or less. In another example, the separation distance Z between the grip members 18 and 20 may be between about 2 and about 4 millimeters. In one embodiment, a separation distance Z between the grip members 18 and 20 may be about 3 millimeters.

Figure 4:
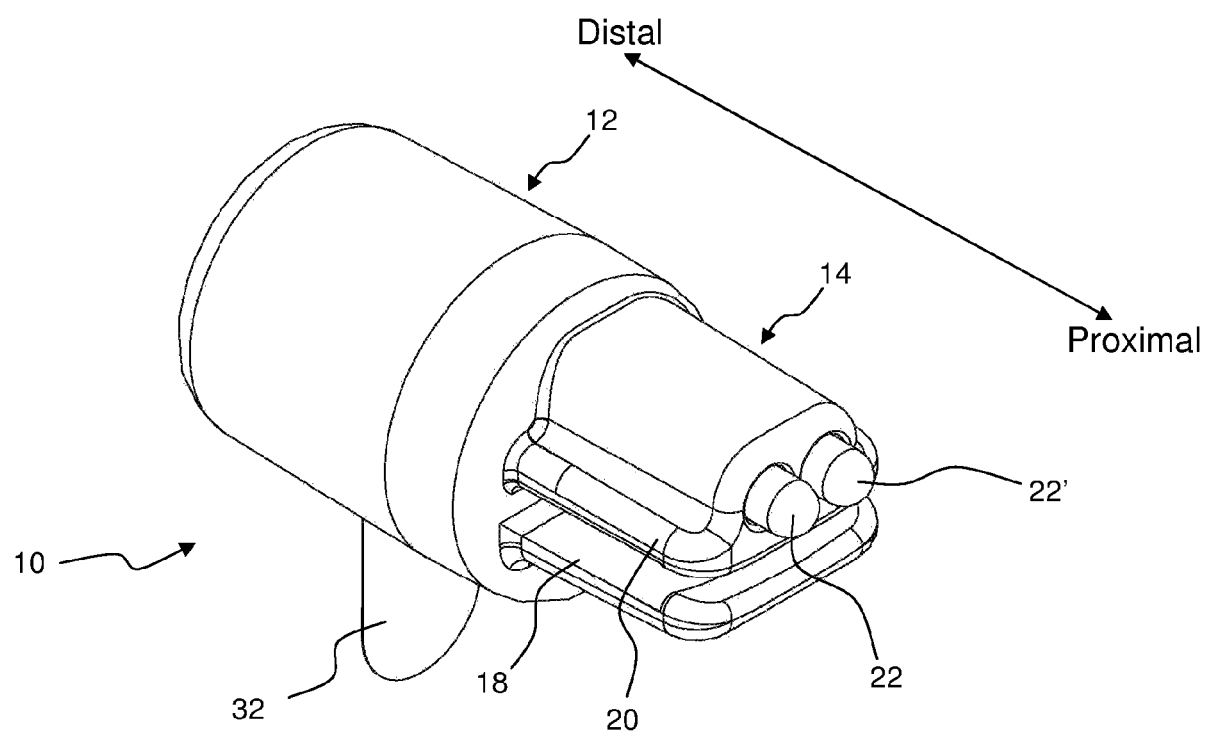
FIG. 4 contains a perspective view of one embodiment of a disposable medical-examination light that comprises two LEDs.

As previously mentioned, the disposable examination light 10 may also have at least one LED. Any known or novel LED 22 suitable to provide light to an internal cavity may be used in the disposable light 10. Furthermore, the LED 22 may have any desired characteristic that allows the LED be disposed in the disposable light 10 and to provide light to a desired area. For example, the LED 22 may be of any size, shape, color, etc., or may produce any wavelength, frequency, intensity, number of lumens, etc. For instance, the disposable light 10 may include a monochromatic or compound LED, such as a bi-color LED. Further, FIG. 4 depicts that the disposable light 10 may have LED 22 and 22'.

Although the LED(s) may produce any desired wavelength of light, in some embodiments, the LED 22 may produce a white light, or a light that has a balanced relative intensity in the visible light spectrum. In some embodiments, the LED 22 may produce a substantially green light that may be between the wavelength of about 475 nanometers and about 575 nanometers. Furthermore, in the case of a bi-color LED, the LED may be switched between producing a white and a substantially green light. Even though many types of LEDs may be used to produce these colors, one or more commercially available, high brightness, high efficiency LEDs may be desirable.

The use of one or more LEDs in the disposable light may provide several benefits over some other conventional light sources. For example, the LED 22 may produce a brighter and/or whiter light that may provide truer color visualization of an internal cavity than do some other conventional lights, which may provide a dull yellow, low intensity light. Thus, the LED 22 may allow better visualization with less strain on the user. Similarly, an LED that produces green light may allow for better visualization of some characteristics of an interior cavity than may another color light. Also, the LED 22 may not produce as much heat as other light sources and may be moved closer to the lighted area than can some other light sources. Further, the LED 22 may require the same or less power to operate than other conventional light sources. Additionally, the LED 22 may be less expensive than many other conventional light sources and may, therefore, be more disposable than some other light sources.

As mentioned, the disposable light 10 may also have a power source to provide power to one or more LEDs. Although any type of power source suitable for use with the disposable light 10 may be used to power the LED(s) 22, in some embodiments, the power source may comprise one or more batteries. Moreover, any type of battery suitable to power the LED 22 may be used with the light 10. In one non-limiting embodiment, the disposable light 10 includes one or more non-rechargeable, or disposable, battery(s) suitable for powering one or more LEDs. Also, as depicted in FIG. 1, the disposable light 10 may use any type of low cost, commercially available button-cell 30, hearing aid, or watch type battery. For example, FIG. 1 illustrates that three, round, 1.5 volt, button-cell batteries 30, 30', and 30" may be used to power the LED 22. Nevertheless, the skilled artisan will understand that the disposable light 10 may include more or less batteries of higher or lower voltages, depending on the desired application.

The disposable light 10 may also have electrical components that are configured to connect the LED 22 to the power source. Indeed, any component or components that may serve to connect the LED 22 to the power source may be incorporated into the disposable light 10. For example, one or more conductive materials, such as metal wires or strips, may be used to connect the positive 56 and negative faces 58, or terminals, of the one or more batteries (e.g., 30, 30', and/or 30") to the LED 22.

FIG. 1 depicts that, in some embodiments, metal wires 26 and 28 may serve as electrical components that may connect the LED 22 with a power source. FIG. 1 illustrates that the wire 26 may extend distally from the LED 22 and be bent to have a contact surface 60, which may connect the LED 22 to the positive face 56 of a battery 30. Similarly, FIG. 1 further depicts that, in some embodiments, the wire 28 of the LED 22 may extend distally from the LED 22 and be bent to have a contact surface 62, which may be used to connect the LED 22 to negative face 58 of the battery 30".

Where the wires 26 and 28 are bent to form contact surfaces 60 and 62, the wires 26 and 28 and/or their corresponding contact surfaces may act as springs so as to contact a battery and/or to keep multiple batteries in contact with each another. Nevertheless, the disposable light 10 need not use the wires 26 and 28, and their contact surfaces as springs. For example, the disposable light 10 may have a coil spring (not illustrated in the Figures), which may be connected to the wire 26 or wire and may serve to close a circuit between the LED and any battery(s) (e.g., 30, 30', and 30").

As previously stated, the disposable examination light 10 may further include a switching mechanism. While any desired switching mechanism may be incorporated with the disposable light 10, in some embodiments, the incorporated switching mechanism may be configured to close an electrical circuit between the batteries 30, 30', and 30" and the LED 22. Indeed, any switching mechanism suitable to close the electrical circuit between the power source and the LED 22 may be used in the disposable light 10. Some non-limiting examples of suitable switching mechanisms may include a slide switch, a toggle switch, a push-button switch, a pressure switch, and a pull-tab that serves to close the electrical circuit between the LED 22 and the power source.

FIG. 1 illustrates that, in some embodiments, the switching mechanism may comprise a pull tab 32 made from any non-conductive material, such as a plastic film. The pull tab 32 may be removably placed in any location sufficient to break the circuit between the power source and the LED(s) 22. For example, the pull tab 32 may be removably placed between two batteries (e.g., between batteries 30 and 30', or between batteries 30' and 30") so that the batteries are not electrically connected. Similarly, the pull tab 32 may be removably placed between the electrical contact surface 60 and the positive face 56 of battery 30. Moreover, the pull tab 32 may be placed between the electrical contact surface 62 and the negative face 58 of battery 30. When desired, the pull tab 32 may be removed by the user and, thereby, close the electrical circuit between the LED 22 and the power source. Thus, the disposable light 10 may be switched on by removing the pull tab 32. In some embodiments, the pull tab 32 may not necessarily be reinserted to break the circuit and switch the disposable light 10 off. Thus, in some embodiments, the disposable light may not be switched off after it has been switched on.

In addition to the previously mentioned components, the disposable light 10 may have any other known or novel component. For example, in embodiments where the disposable light 10 comprises more than one LED, any known or novel switching mechanism may be used to switch between powering the various LEDs. For instance, in embodiments of the disposable light 10 that comprise a white light producing LED and a green light producing LED, a switching mechanism may be used to switch between powering the white light and the green light producing LED. For instance, the light may include a slide switch, such as a single pull double throw, or other switching mechanisms known in the art.

As another example of an additional component that may be incorporated with the disposable light 10, FIG. 1 illustrates that the light 10 may include a non-conductive sleeve 64. The non-conductive sleeve 64 may be disposed around the wire 26 or the wire 28 of the LED 22 to provide electrical insulation and prevent unintended contact with the power source.

Each of the aforementioned components may be made from materials suitable for use in a disposable medical examination light 10. Indeed, because the entire disposable light 10 may be discarded after a single use, each component of the light 10 may also be disposable, or be sufficiently inexpensive so as to allow the components to be discarded after a single use. For example, the casing 12, protrusion 14, grip members 18 and 20, non-conductive sleeve 64, and/or pull tab 32, may be made from commercially available polymeric materials, including but not limited to nylon, polyethylene, polyurethane, polyvinyl chloride, mixtures and composites thereof. Additionally, the batteries (e.g., 30, 30', and 30") and/or LED 22 may be made from environmentally safe materials, so as to be disposable and/or recyclable.

The disposable light 10 may be made using any known method or technique. For example, the protrusion 14, grip members 18 and 20, and the casing 12 may be molded or fabricated as known in the art. Furthermore, in some embodiments, the protrusion 14, grip members 18 and 20, and the casing 12, may be formed from the same material. For instance, FIG. 1 depicts that the proximal portion 38 of the casing 12, the protrusion 14, and grip members 18 and 20 may be formed from the same materials and may be formed together as a single unit. Nevertheless, in other embodiments, the casing 12, protrusion 14, and grip members 18 and 20 may be formed separately and/or from different materials. Additionally, the various components may be attached to each other through any known or novel method or technique. For example, the proximal portion 38 and the distal portion 40 may be attached to each other, or the grip members 18 and 20 and the protrusion 14 may be connected to the casing 12, through any form of mechanical attachment, including but not limited to, frictional engagement, adhesive bonding, and/or heat sealing.

The disposable light 10 may also be used in any manner suitable to provide light to a desired area. However, in order to better explain the described disposable light 10 a non-limiting example of the light's use with a speculum 70 is provided herein. In this example, the disposable light 10 may be manufactured with a pull tab 32 removably inserted so as to break the electrical connection between the power source and the LED 22.

When desired, the pull tab 32 may be removed so as to close the electrical circuit between the power source and the LED 22. In this manner, the disposable light 10 may be switched on and the LED 22 may produce light to illuminate an interior cavity. Similarly, in this example, where the disposable light has two LEDs (as in FIG. 4), removing the pull tab 32 may serve to provide power to one LED 22 which may be used to light the desired area. Furthermore, the power source may be switched to power the other LED 22' as described hereinafter.

Before or after the disposable light 10 has been turned on, the disposable light 10 may be attached to a speculum 70. FIG. 3 illustrates that the disposable light 10 may be attached to the distal end 74 of the speculum blade 76 so that the protrusion 14 extends into the visual/working field 72 of the speculum 70. In order to attach the disposable light 10 to the speculum 70, the disposable light 10 may be pushed against the distal end 74 of a speculum blade 76 so that the blade 76 is located between the first grip member 18 and the second grip member 20. Upon attachment, the distal end 74 of the blade 76 may be disposed adjacent the proximal surface 16 of the casing 12. A frictional engagement on one or both of the grip members 18 and 20, such as the barb 54 (depicted in FIG. 1), may then retain the distal end 74 of the speculum blade 76 between the grip members while the speculum 70 is used, as shown in FIG. 3.

During the use of the speculum 70, the disposable light 10 may provide light to the interior cavity. Additionally, in embodiments with more than one LED or an LED that produces more than one color of light, a switching mechanism may be used to switch between powering the various LEDs or certain colors of a bi-color LED at any time. For instance, in a disposable light 10 with both a green light producing and a white light producing LED (as illustrated by 22 and 22' in FIG. 4), a switching mechanism may be used to switch between the green and the white light producing LED, and thereby provide a better or differential visualization of the lighted area.

Additionally, when the speculum 70 is removed from the interior cavity, the disposable light 10 may be pulled from or otherwise removed from the speculum 70. Once removed, the disposable light 10 may be discarded in any conventional method. For instance, the disposable light may be placed in a medical waste receptacle for suitable disposal.

Moreover, the present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the forgoing description. All changes that come within the meaning and range of equivalency of the claims are to be embraced within their scope.

The invention claimed is:

1. A disposable medical-examination light, wherein the examination light comprises:
   a casing that comprises an interior and an exterior, the interior being adapted to hold at least one battery and the exterior comprising a proximal surface and a distal surface, wherein the proximal surface comprises a protrusion that extends from the proximal surface;
   a gripping mechanism extending from the proximal surface to removably attach the disposable examination light to a medical device;
   at least one light-emitting diode that is disposed at a proximal end of the protrusion;
   electrical components for connecting the at least one battery to the at least one light-emitting diode; and
   a switching mechanism configured to close an electrical circuit between the at least one battery and the at least one light-emitting diode.

2. A disposable medical-examination light, wherein the examination light comprises:
   a casing that comprises an interior and an exterior, the interior being adapted to hold at least one battery and the exterior comprising a proximal surface and a distal surface, wherein the proximal surface comprises a protrusion that extends from the proximal surface, wherein the protrusion extends less than about 8 millimeters into a visual/working field of a speculum;
   a gripping mechanism extending from the proximal surface;
   at least one light-emitting diode that is disposed at a proximal end of the protrusion;
   electrical components for connecting the at least one battery to the at least one light-emitting diode; and
   a switching mechanism configured to close an electrical circuit between the at least one battery and the at least one light-emitting diode.

3. The disposable medical-examination light of claim 2, wherein the gripping mechanism comprises a first resilient grip member that opposes an adjacent second grip member formed on the protrusion.

4. The disposable medical-examination light of claim 3, wherein the first and second grip members comprise a frictional engagement.

5. The disposable medical-examination light of claim 4, wherein the frictional engagement comprises a barb.

6. The disposable medical-examination light of claim 1, wherein the switching mechanism comprises a removable pull tab that closes the electrical circuit upon removal.

7. The disposable medical-examination light of claim 1, wherein the at least one light-emitting diode produces white light.

8. The disposable medical-examination light of claim 1, wherein the at least one light-emitting diode produces green light.

9. The disposable medical-examination light of claim 1, wherein the at least one light-emitting diode is a bi-color light-emitting diode.

10. The disposable medical-examination light of claim 9, wherein the bi-color light-emitting diode produces a white light and a green light.

11. The disposable medical-examination light of claim 9, further comprising a switching mechanism to switch between producing the white light and the green light.

12. The disposable medical-examination light of claim 1, wherein at least one light-emitting diode produces white light and another light-emitting diode produces green light.

13. The disposable medical-examination light of claim 12, further comprising a switching mechanism to switch between powering the light-emitting diode producing white light and the light-emitting diode producing green light.

14. The disposable medical-examination light of claim 1, wherein the gripping mechanism is sized and configured to attach to a vaginal speculum.

15. A disposable speculum light, comprising:
   a casing that comprises an interior and an exterior, the interior being adapted to hold at least one battery and the exterior comprising a proximal surface and distal surface, wherein the proximal surface comprises a protrusion that extends from the proximal surface and extends less than about 8 millimeters into a visual/working field of a speculum;
   a gripping mechanism extending from the proximal surface, wherein the gripping mechanism comprises a first resilient grip member that opposes an adjacent second grip member formed on the protrusion, and wherein the first and second grip members comprise a frictional engagement;
   at least one light-emitting diode that is disposed at a proximal end of the protrusion;
   electrical components for connecting the at least one battery to the at least one light-emitting diode; and
   a switching mechanism comprising a removable pull tab that is configured to close an electrical circuit between the at least one battery and the at least one light-emitting diode upon removal of the pull tab by a user.

16. The disposable speculum light of claim 15, wherein the frictional engagement comprises a barb.

17. The disposable speculum light of claim 15, wherein the at least one light-emitting diode produces white light.

18. The disposable speculum light of claim 15, wherein the at least one light-emitting diode produces green light.

19. The disposable speculum light of claim 15, wherein at least one light-emitting diode produces white light and another light-emitting diode produces green light.

20. The disposable speculum light of claim 15, further comprising a switching mechanism to switch between powering the light-emitting diode producing white light and the light-emitting diode producing green light.

21. The disposable speculum light of claim 15, wherein the casing further comprises a proximal portion and a distal portion.

22. The disposable speculum light of claim 15, wherein the interior of the casing is substantially cylindrical.

23. The disposable speculum light of claim 15, wherein the exterior of the casing is substantially cylindrical.

* * * * *